United States Patent [19]

Appling et al.

[11] Patent Number: 5,651,776
[45] Date of Patent: Jul. 29, 1997

[54] LUER-TYPE CONNECTOR

[75] Inventors: William M. Appling, Hartford; Kurt E. Greenizen, Lake George; Daniel K. Recinella, Queensbury, all of N.Y.

[73] Assignee: AngioDynamics, Inc., Queensbury, N.Y.

[21] Appl. No.: 408,217

[22] Filed: Mar. 22, 1995

[51] Int. Cl.$^6$ ................................................. A61M 25/00
[52] U.S. Cl. ........................ 604/283; 604/905; 285/332; 285/354
[58] Field of Search ........................ 604/280–283, 604/240, 243, 905; 285/177, 332, 354, 355, 386, 390

[56] References Cited

U.S. PATENT DOCUMENTS

| | | | |
|---|---|---|---|
| 2,562,294 | 7/1951 | Cahenzli, Jr. | 285/157 |
| 3,876,234 | 4/1975 | Harms | 604/283 X |
| 4,046,479 | 9/1977 | Paley | 403/306 |
| 4,735,441 | 4/1988 | Stephens | 285/332 X |
| 4,893,844 | 1/1990 | Chelette et al. | 285/113 |
| 5,078,433 | 1/1992 | Morse et al. | 285/281 |
| 5,156,421 | 10/1992 | Chauvel | 285/354 X |
| 5,509,911 | 4/1996 | Cottone, Sr. et al. | 604/283 |

FOREIGN PATENT DOCUMENTS

2024974  1/1980  United Kingdom.

*Primary Examiner*—Sam Rimell
*Assistant Examiner*—Robert V. Racunas
*Attorney, Agent, or Firm*—McAulay Fisher Nissen Goldberg & Kiel, LLP

[57] ABSTRACT

A luer-type adapter has a dual instead of a single set of engaging screw threads. A proximal and a distal screw thread on the hub engage proximal and distal screw threads on the collar of the connector to provide at least twice the engaging or sealing force between the tapered surfaces of the stem and hub which are forced together by rotating the collar relative to the hub to engage the two sets of threads. The diameters of the engaging distal screw threads have to be sufficiently great so that the proximal screw thread on the hub can pass under the distal screw thread on the collar in order to effect proximal as well as distal engagement. An O-ring mounted on an untapered distal segment of the stem engages an untapered inner hub surface to provide additional sealing force which is particularly useful where gas is being provided through the adapter.

15 Claims, 9 Drawing Sheets

LUER-TYPE CONNECTOR

BACKGROUND OF THE INVENTION

The present invention is related to a connector for coupling a source of a liquid or gas to a catheter line or other medical device that is used with a patient.

Figure 1:
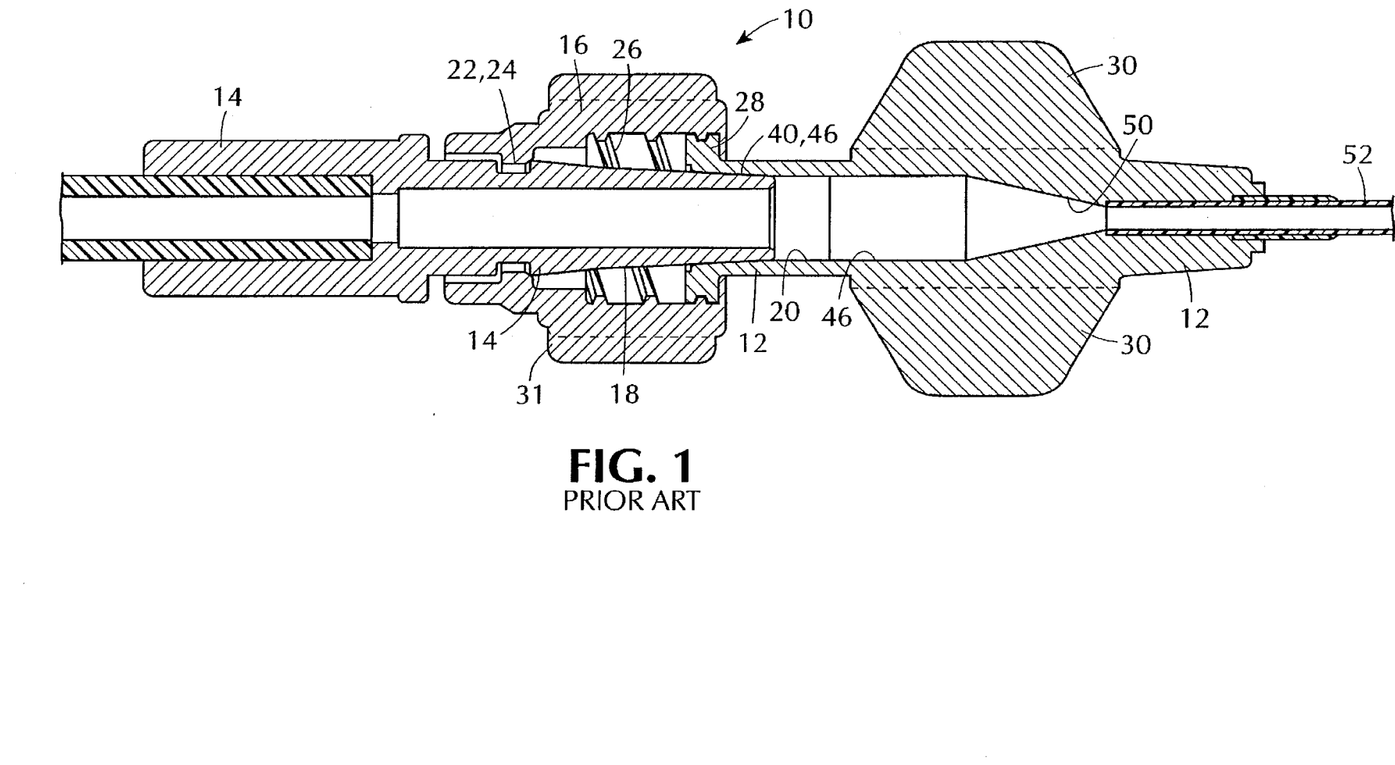
FIG. 1 is a longitudinal sectional view of an assembled adapter of the prior art illustrating a standard luer coupling.

Luer connectors and luer-type connectors are well known in the medical appliance field. An example of such is shown in FIG. 1 of the drawings. They are used to provide a large surface area sealing zone between a catheter hub and the stem of a connector. This sealing zone entails the engagement of gently tapered tubular surfaces which are forced longitudinally against one another by a threaded arrangement, external to the sealing surfaces, between the hub and the connector. The threaded arrangement provides a quick connect and quick disconnect feature that facilitates use by medical personnel. Luer connectors are employed in medical procedures to connect a source of a liquid to catheters to supply the liquid under slightly raised pressures. For example, during infusion processes, liquids are delivered using a pressure which ranges between 5 p.s.i. and 10 p.s.i.

At times it is important to deliver a liquid to the catheter under relatively high pressure. For example, during a liquid contrast procedure in radiology, liquids are delivered at pressures that are in the range of 1,200 p.s.i. At these pressures, currently available standard luer adapters and connectors are likely to fail and in particular to separate under high pressure with the result that the liquid leaks and pressure is lost. A linden luer lock can be used in which a multiple turn of a threaded stem into a collar is used to establish a seal that can withstand these pressures. But a linden lock does not provide the quick connect feature of a typical luer lock.

Some medical procedures call for delivery of a gas through a catheter. For example, inflation of a balloon in the vascular system may require delivery of oxygen or some other gas at a pressure in the range of 300 p.s.i. The available catheter hubs and connectors are designed for delivery of liquids and are unreliable for the delivery of gas. The seal between the two tapered surfaces of the stem of the connector and of the hub is generally inadequate to prevent escape and/or contamination of the gas being delivered.

Accordingly, it is a major purpose of this invention to provide a medical connector and adapter for use with items such as catheters which will provide a quick connect and quick disconnect feature yet retain its sealing integrity under relatively high liquid pressures.

It is another purpose to provide a connector and adapter which can be used to couple gas to a catheter or other medical delivery apparatus.

It is a further purpose of this invention to provide the above objectives with a device and design that can be readily adapted to presently known procedures and that does not require either extensive or expensive additional sealing equipment.

It is a further and related purpose of this invention to provide such an improved sealing adapter which is easy to use and which preferably involves procedures with which medical personnel are familiar.

BRIEF DESCRIPTION

An adapter is composed of a hub to which a collar and stem are connected. The hub is typically the proximal end of a catheter. The stem and hub have a longitudinal bore in communication through which fluid is delivered from stem to hub to catheter. The stem has a segment with a tapered outside surface which extends into the hub and mates with a tapered inside surface of the hub. Thus when the hub and stem are drawn together longitudinally, the two tapered surfaces engage to form a tight seal to prevent fluids that flow through the stem and hub from escaping.

In one embodiment, the outer surface of the hub has first and second longitudinally spaced threads which engage first and second threads on the inner surface of a collar which rotates on the stem. When the collar is rotated, both sets of threads engage to force the two tapered surfaces tightly together. The use of two sets of threads instead of a single thread at least doubles the force for holding the two tapered surfaces together.

In order to permit the hub to be inserted over the stem and within the collar, the collar thread nearest the collar opening has a crest diameter great enough to permit the first thread on the hub to pass under it so that the first hub thread will engage the first or more interior thread on the collar. The hub then has a larger diameter second thread to engage the larger diameter second thread of the collar.

Thus the smaller diameter threads on the hub and collar are positioned around a large diameter zone of the two tapered surfaces while the larger diameter threads of the collar and hub are positioned around a smaller diameter zone of the two tapered surfaces.

The hub threads are typically a short threaded annular disc and are positioned to engage the collar threads so that full tapered surface engagement occurs in about 180 degrees of rotation of the collar on the hub. Thus the quick connect and disconnect feature of the traditional luer adapter is retained.

In addition, an O-ring seal on the outside surface of an untapered zone on the stem engages an interior untapered surface of the hub to provide a more effective seal for circumstances where gas under pressure is being fed through the stem and hub.

The collar and stem constitute a connector separable from the hub. The connector and hub in combination constitute the adapter. The connector can be a two piece collar and stem in which the collar rotates on the stem or the connector can be a one piece unit where the connector and hub have to rotate relative to each other to effect thread engagement.

DESCRIPTION OF THE PREFERRED EMBODIMENTS

Figure 3:
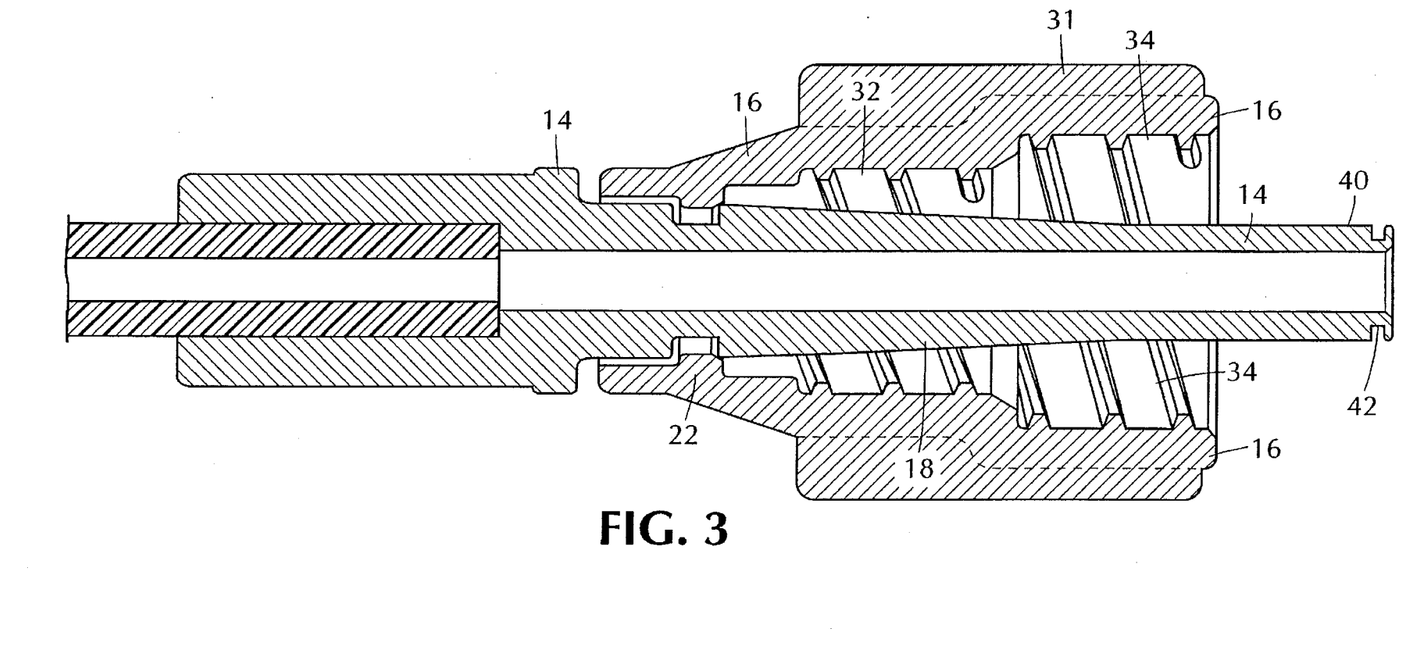
FIG. 3 is a longitudinal sectional view similar to that of FIG. 2 showing only the collar and stem, which constitute the connector portion of the adapter of the FIG. 2 embodiment.

FIG. 1 shows a typical luer locking adapter 10. The adapter is composed of three major elements; a hub 12, a stem 14 and a collar 16. The luer fitting is the engagement between a tapered outer surface 18 of the stem and a tapered inner surface 20 of the hub. These two surfaces show engagement in FIG. 1 and are seen more clearly in FIGS. 3 and 4 which are separate views of the comparable elements in an embodiment of this invention. The stem 14 and collar 16 combination is called a connector. In some designs, the stem and collar are a single integral unit. The standard luer type is 6%; i.e., 0.060 inches per inch on diameter.

In the FIG. 1 example, the collar 16 is mounted for rotational movement about the stem 14 by virtue of an annular collar rim 22 that is snapped into an annular stem groove 24. The inner surface of the collar 16 is spaced from the tapered outer surface 18 of the stem. The inner surface of the collar is threaded with screw threads 26. The end of the hub 12 that is inserted into the collar 16 has screw threads 28 which engage the collar screw threads 26.

It is important in a luer coupling, or in one that uses the luer approach, that the tapered outer surface 18 of the stem 14 and tapered inner surface 20 of the hub 12 have exactly the same taper so that they will mate with one another and effect a large area seal so that fluid flowing through the adapter 10 will not leak. When the hub 12 is assembled over the stem 14, the tapered surfaces 18 and 20 contact at the point where the hub thread 28 engages the collar thread 26. The collar 16 is then rotated in the appropriate direction to cause the threads to engage and thereby force the two surfaces 18 and 20 tightly against one another. Typically the screw thread 28 on the hub 12 is a half turn of thread on an annular disc. The threads 26 and 28 are longitudinally positioned relative to the engaging tapered surfaces 18 and 20 so that a 180 degree turn of the collar 16 effects the desired seal.

Most of the portions of each component shown in FIG. 1 are annular. Significant exceptions are two wings 30 on the hub and four wings 31 on the collar which facilitate gripping by a user.

The primary application of this invention is for use with medical instruments such as a catheter in which the hub 12 is connected to a catheter and the connector (stem and collar) are to provide connection to a source of fluid. Thus it will facilitate discussion to refer to elements of the arrangement as being distal or proximal to one another. That is, a first element that is more distal than a second element means that the first element is intended to be placed further into the body of a patient than is the second element.

FIGS. 2 through 9 show one embodiment of this invention in considerable detail. Although aspects of the hub, stem and collar in the embodiment of the invention differ from aspects of the standard hub, stem and collar that is shown in the FIG. 1 prior art device, the same reference numerals will generally be used in order to facilitate understanding. Exceptions include the multiple thread arrangement which is at the heart of this invention and wherein the departure from the prior art with respect to those features is substantial.

The important thing to note about the embodiment shown in FIGS. 2 through 9 is that there are first and second threads 32 and 34, respectively, on the inner surface of the collar 16 and that there are first and second threads 36 and 38, respectively, on the proximal portion of the hub 12. The threads 32 and 34 on the collar are most clearly shown in the longitudinal cross-section of FIG. 3. The threads 36 and 38 on the hub are clearly seen in FIG. 4 and FIG. 9.

In order for the proximal thread 36 on the hub 12 to engage the proximal thread 32 in the collar 16, the hub 36 must pass under the distal thread 34 of the collar without being obstructed. Accordingly, it is essential that the crest diameter of the hub thread 36 be less than the crest diameter of the distal collar thread 34. Since there is a distal hub thread 38 that engages the distal collar thread 34, this means that the crest of the first hub thread 36 has to be less than the root of the second hub thread 38. Since the first or proximal hub thread 36 has to engage the first or proximal collar thread 32, it follows that the root diameter of the proximal collar thread 32 has to be less than the crest diameter of the distal collar thread 34.

It is further important that both sets of threads engage simultaneously and effect the full sealing of the tapered surfaces 18 and 20 in a half turn. This will assure retaining the quick connect and quick disconnect function of known luer connectors and provide an operating effect with which medical personnel are familiar. Thus the spacing between the leading edges of the hub screws 36 and 38 should equal the spacing between the leading edges of the collar screws 32 and 34. The lead of the screw threads should be in alignment to effect simultaneous engagement.

Figure 4:
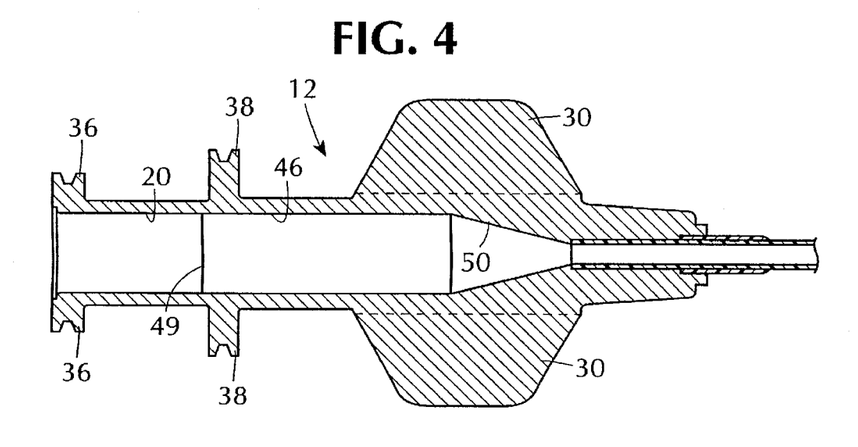
FIG. 4 is a longitudinal sectional view similar to that of FIG. 2 of the hub portion of the FIG. 2 adapter.
Figure 5:
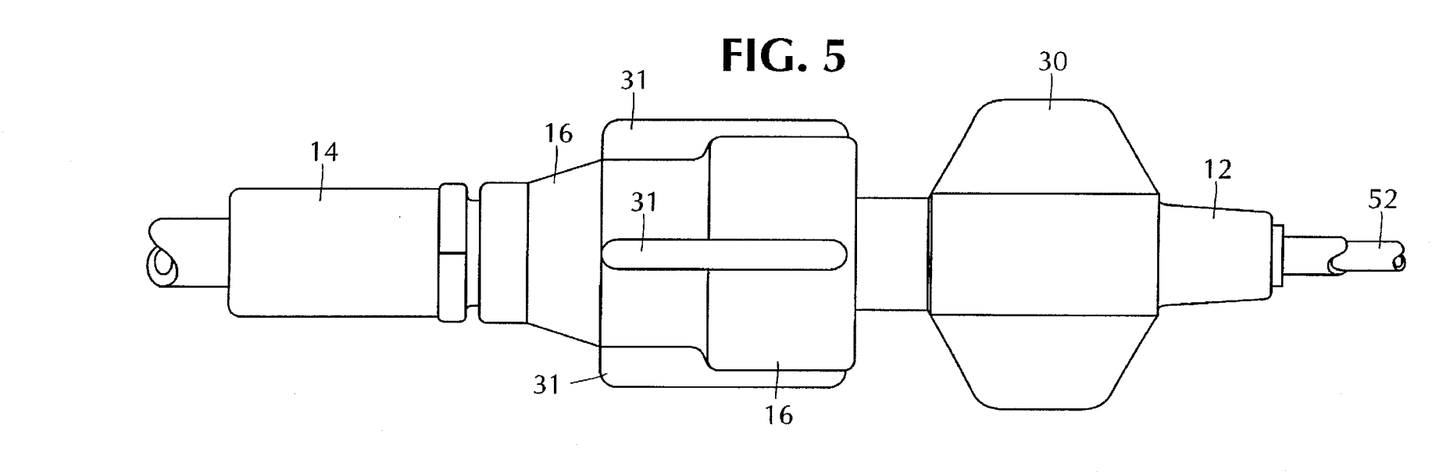
FIG. 5 is an elevation view of the FIG. 2 adapter.

In one embodiment, the first or proximal threads 32 and 36 are designed to have a standard diameter used in comparable luer connectors so that, depending on other dimensional parameters of the equipment involved, the FIG. 4 hub of this invention could be coupled to a standard connector such as the connector 14, 16 shown in FIG. 1.

Figure 2:
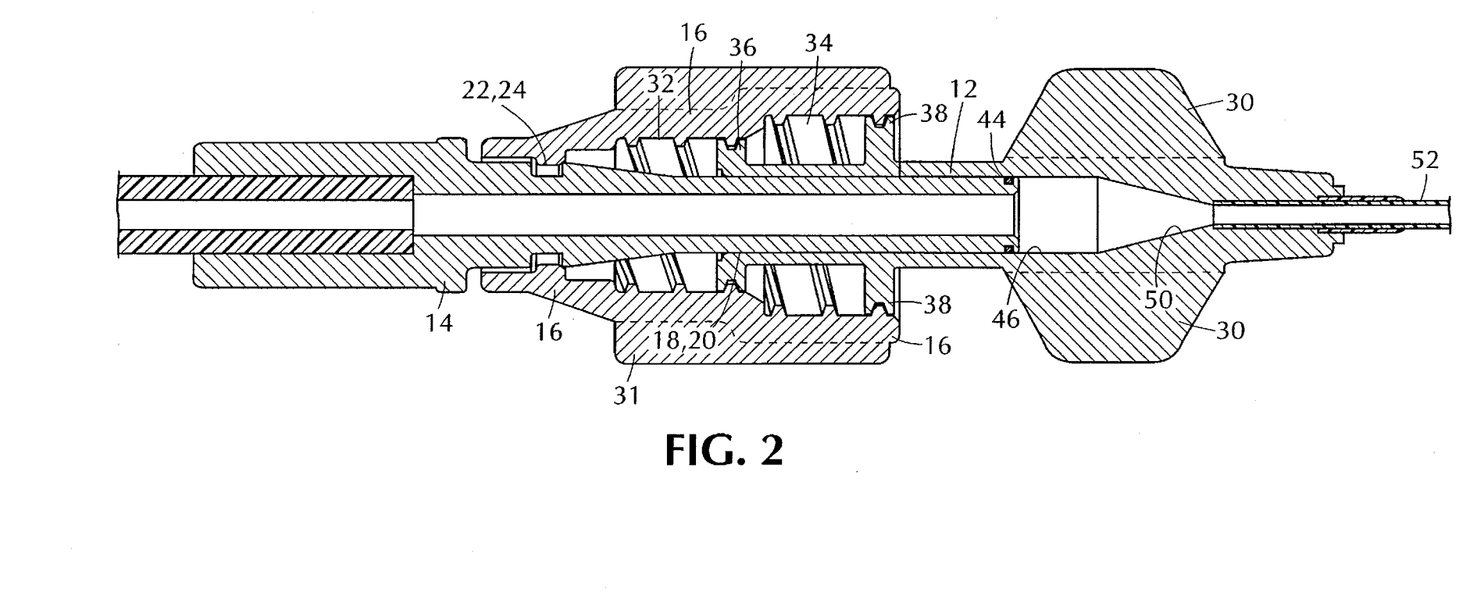
FIG. 2 is a longitudinal sectional view of an assembled adapter illustrating a first embodiment of the invention.
Figure 6:
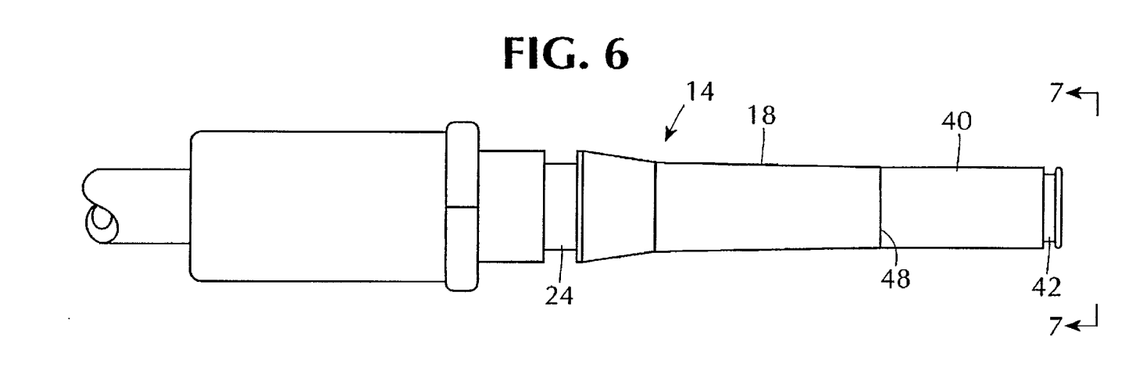
FIG. 6 is an elevation view of the stem of the FIG. 2 adapter.
Figure 7:
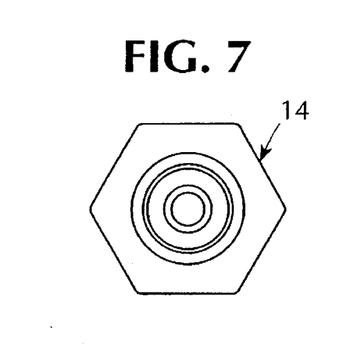
FIG. 7 is an end view along the plane 7—7 of the FIG. 6 stem.
Figure 8:
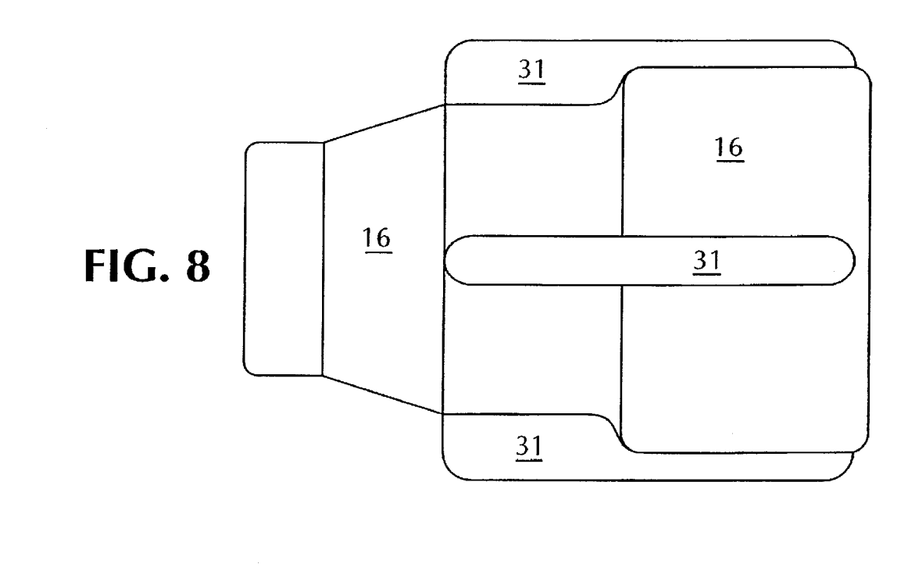
FIG. 8 is an elevation view of the collar of the FIG. 2 adapter.
Figure 9:
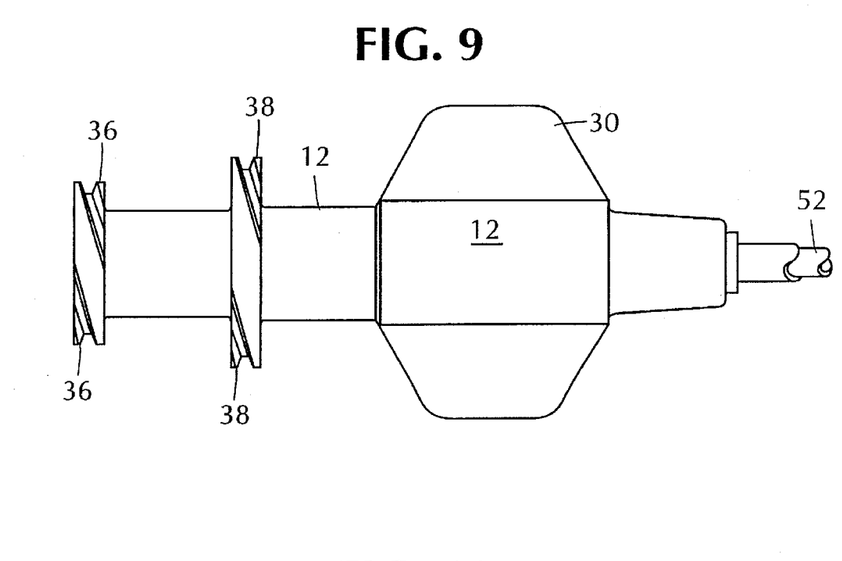
FIG. 9 is an elevation view of the hub of the FIG. 2 adapter.

As may best be seen in FIG. 6, the distal end of this stem 14 contains a non-tapered portion 40 which terminates in an annular groove 42. Within that annular groove 42, there is an O-ring 44. As shown in FIG. 2, the O-ring 44 engages a non-tapered zone 46 of the inner surface of the hub 12.

As may best be seen in FIG. 4, the tapered surface of the hub 20 extends distally only to an area approximately at the screw thread 38. The inner surface zone 46 is not tapered and is the surface which is engaged by the O-ring 44 in the groove 42. In order to assure that the non-tapered zone 40 on the stem 14 will not bind against the tapered zone 20 of the hub, it is important that the tapered zone 18 of the stem extend past the end of the tapered zone 20 of the hub. Thus, when assembled it is important that the line 48 on the stem be distal of the line 49 on the hub. There is a hub zone 50 which is distal of the untapered zone 46. The zone 50 tapers sharply down toward the diameter of the catheter 52.

The combination of the double threaded arrangement and the O-ring provides a particularly effective sealing arrangement. The double threaded engagement means that at least twice the force becomes available to hold the two tapered surfaces 18 and 20 together. Because the second or distal threads 34, 38 have a larger diameter, the actual additional force is somewhat greater than twice what would be available with a single standard luer-type of engagement. The O-ring 44 seal in combination with the more than doubling of the engaging force between the two tapered surfaces 18 and 20, provides a much enhanced sealing arrangement thereby permitting the adapter of this invention to be used with gasses and with liquids under significant pressure.

In one embodiment, the distance between the leading edges of the two hub threads is 0.295 inches and the distance between the leading edge of the two collar threads is the same. In that embodiment, the taper is a standard six percent taper (that is, 0.060 inches per inch on a diameter). The stem taper zone 18 is 0.425 inches and the tapered zone 20 of the hub 12 is 0.286 inches. In that embodiment, the untapered portion 40 of the stem, including the O-ring, to the distal end is 0.33 inches while the untapered portion 46 of the hub is over 0.45 inches. In that embodiment, the hub threads 36 and 38 are both double threads, each having approximately 180 degree turn. The first or smaller hub thread has a crest diameter of 0.306 and a root diameter of 0.265 inches while the larger more distal hub thread 38 has a crest diameter of 0.405 inches and a root diameter of 0.364 inches. The corresponding diameters of the collar threads are: the first collar thread 32 has a root diameter of 0.313 inches and a crest diameter of 0.279 inches while the larger collar thread 34 has a root diameter of 0.412 inches and a crest diameter of 0.378 inches.

Figure 10:
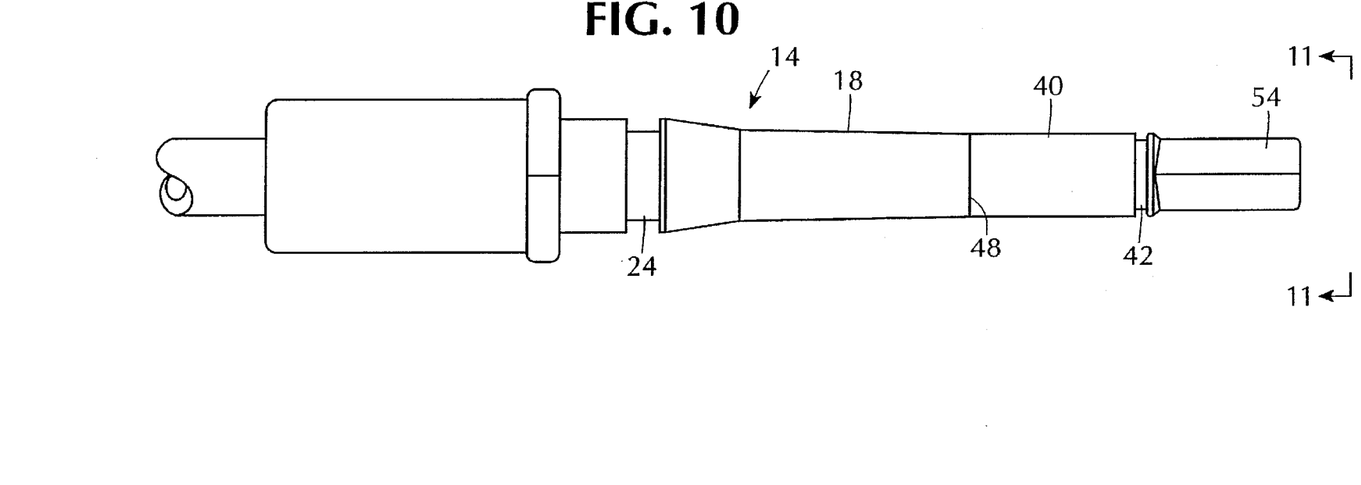
FIG. 10 is an elevation view of the stem of a second embodiment of the invention showing a hexagonal in cross-section extension at the distal end of the stem.
Figure 11:
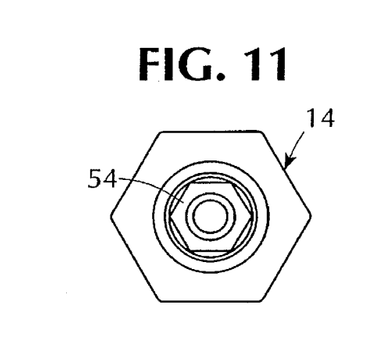
FIG. 11 is an end view along the plane 11—11 of the FIG. 10 stem.
Figure 12:
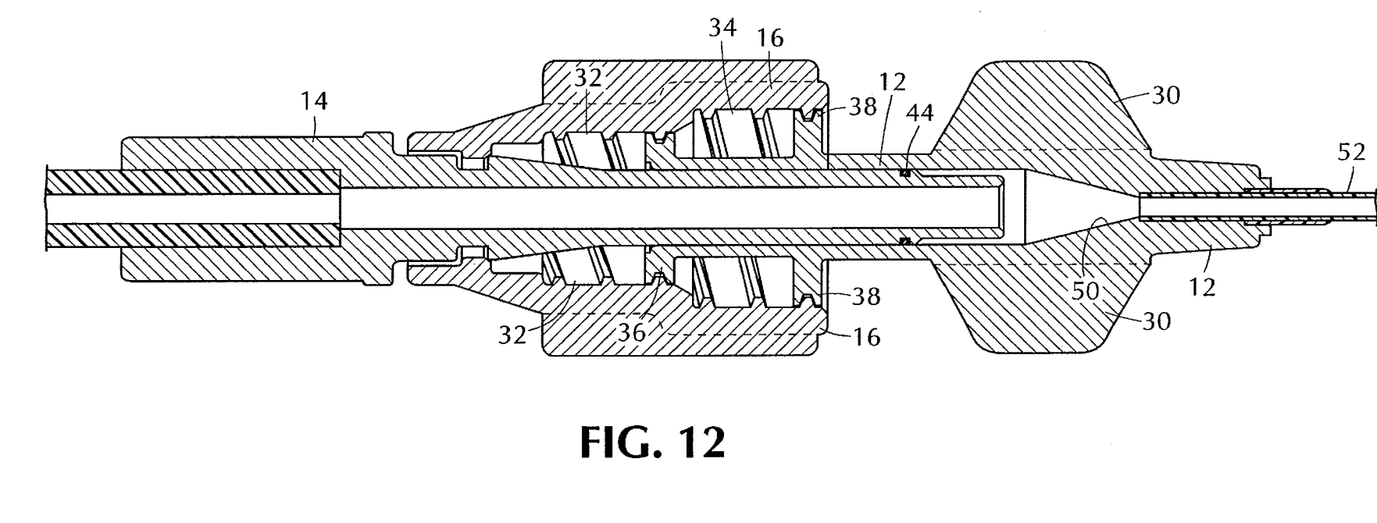
FIG. 12 is a longitudinal sectional view of an adapter employing the FIG. 10 stem.

FIGS. 10 through 12 show a second embodiment which is similar to the embodiment of FIGS. 1 through 9 except that it contains an hexagonal in cross-section distal extension 54 at the end of the stem 14. This hexagonal extension has a maximum diameter equal to that of the untapered zone 40 so that it will slip within the untapered zone 46 of the hub. As may be seen from FIG. 12, the extension 54 essentially has no operating effect. However, the purpose of this extension 54 is so that if a connector (stem and collar) design of this invention is attempted to be assembled with a standard prior art hub, then the extension 54 will project into the sharply tapered zone immediately proximal of the catheter and will make it difficult to assemble. If someone jammed a connector of this invention into a prior art hub, it would be apparent that there is an improper connection because as soon as an attachment is made to a patient, there would be blood leakage because of the body blood pressure.

It would be important in many circumstances that a coupling of a connector of this invention not be made to a prior art hub because selection of the inventive connector would usually be made when it is contemplated that liquid under pressure or gas of some sort is to be administered. In such a circumstance, it is important that the full sealing integrity of this invention be achieved in order to avoid a mishap.

As can be seen in FIG. 12, the O-ring 44 engagement between the straight wall zones 40 and 46 of the stem and hub, respectively, is provided. The length of the straight wall zone 40 and hexagonal segment 54 together has been selected to be at least 0.437 inches because that length was found to be sufficient to assure an inability to connect with most prior art hubs.

Figure 13:
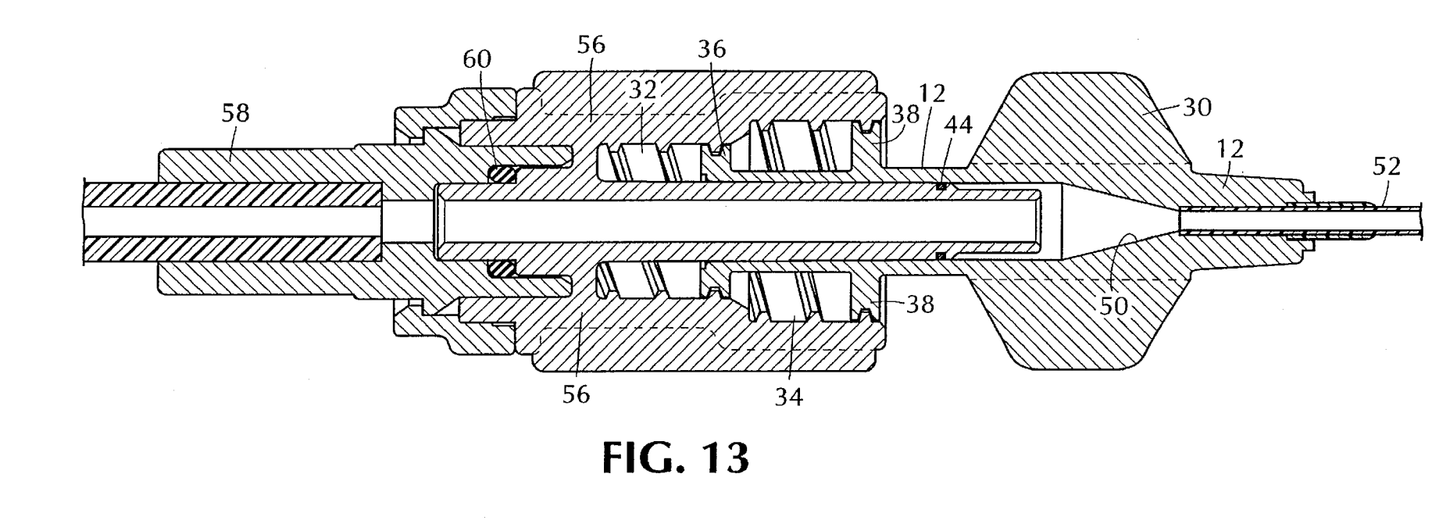
FIG. 13 is a longitudinal sectional view of an adapter illustrating a third embodiment of this invention in which the collar and stem form a single piece, integral connector.

FIG. 13 shows a further modification of the FIGS. 10–12 embodiment in which the collar and stem are an integral element 56 and are mounted to a proximal fitting 58 by means of an O-ring 60 that permits the connector 56 to be rotated to engage the screw threads on the collar and on the hub without requiring that the fitting 58 be rotated.

Figure 14:
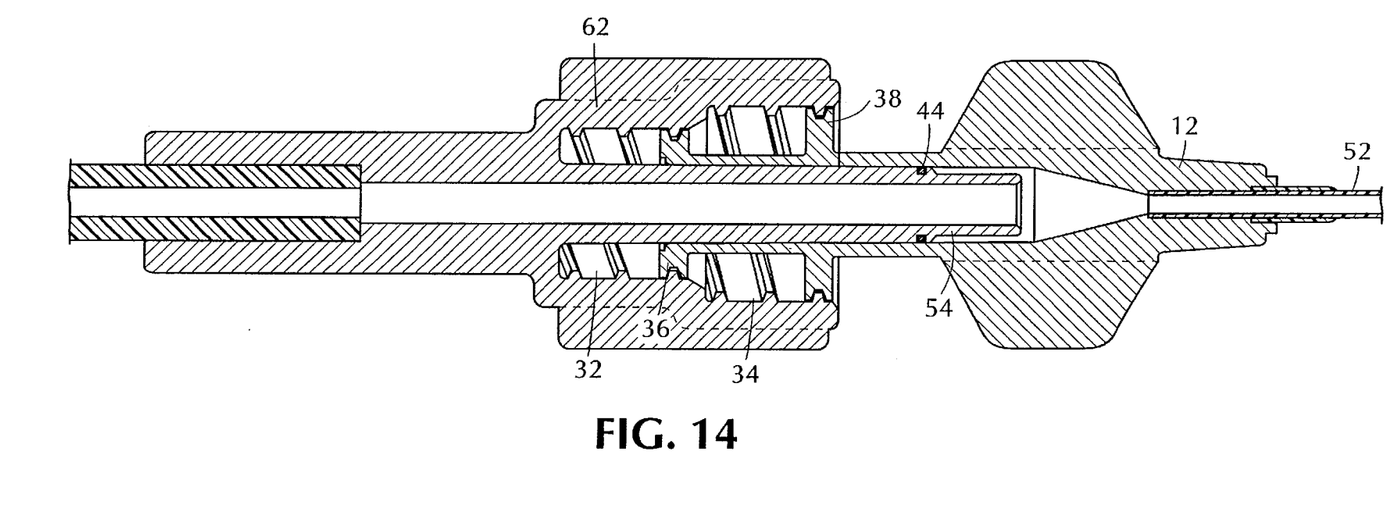
FIG. 14 is a longitudinal sectional view of a fourth embodiment of this invention in which the integral connector is integral with the rest of the proximal fitting.

FIG. 14 shows a further embodiment which also provides for an integral collar and stem 62 that incorporates the entire fitting and would require that the proximal portion of the fitting be rotated together with the collar and stem when connecting to the catheter shown.

Although this invention has been described in connection with a coupling to a catheter, it should be understood that the adapter of this invention would be particularly useful when coupling any high pressure liquid line or any gas source to other medical appliances applied to a patient such as a syringe.

What is claimed is:

1. In a luer-type adapter having engaging tapered surfaces on a mating stem and hub, the mating surfaces being an outer surface of the stem and an inner surface of the hub, and having a collar surrounding the stem, the improvement comprising;

proximal and distal threads on awl inner surface of said collar and proximal and distal threads on an outer surface of said hub, said proximal collar and hub threads being positioned and dimensioned to engage one another, said distal collar and hub threads being positioned and dimensioned to engage one another, the crest diameter of said distal collar thread being greater than the crest diameter of said proximal hub thread, wherein said proximal and distal threads of said hub simultaneously engage said proximal and distal threads of said collar, and said mating stem is sealed with said hub by rotating one of said collar and said hub substantially 180 degrees.

2. The adapter improvement of claim 1 further comprising:

an O-ring mounted on the outer surface of said stem and engaging the inner surface of said hub.

3. The adapter improvement of claim 1 further comprising:

said stem having an untapered surface extending distally of the tapered surface of the stem, said hub having an untapered surface extending distally of the tapered surface of the hub, said untapered surface of said stem extending into said untapered surface of said hub, and an O-ring held on said untapered surface of said stem and engaging said untapered surface of said hub.

4. The adapter improvement of claim 3 wherein:

said untapered surface of said stem includes a segment distal of said O-ring wherein said segment has a non-circular cross-section.

5. The adapter improvement of claim 3 wherein:

the distal end of said tapered surface of said stem extends past the distal end of said tapered surface of said hub.

6. The adapter improvement of claim 4 wherein:

the distal end of said tapered surface of said stem extends past the distal end of said tapered surface of said hub.

7. A luer-type connector comprising:

a tubular stem having an inner surface and an outer surface, said outer surface having a tapered zone, said tapered zone having a proximal diameter that is greater than its distal diameter, a collar portion having an outer surface and an inner surface, said inner surface of said collar portion spaced from and encircling a portion of said tubular stem, said collar having proximal and distal threads on said inner surface, the crest diameter of said distal thread being greater than the root diameter of said proximal thread, and a hub having an outer surface, said hub having proximal and distal threads on said outer surface, wherein said proximal and distal threads of said hub simultaneously engage said proximal and distal threads of said collar, and said tubular stem is sealed with said hub by rotating one of said collar and said hub substantially 180 degrees.

8. The connector of claim 7 further comprising:

an O-ring seal mounted on the outer surface of said stem.

9. The connector of claim 7 further comprising:

said stem having an untapered outer surface zone distal of said tapered zone, and an O-ring seal mounted on said untapered zone of said stem.

10. The connector of claim 7 wherein said collar portion is rotatable on said tubular stem.

11. The connector of claim 7 wherein said stem and collar are integral.

12. A hub for mating with a stem by use of a collar in a lust-type adapter, where said collar includes proximal and distal threads on an inner surface, said hub comprising:

a tubular segment having an outer surface and a tapered inner surface, said tapered inner surface having a proximal diameter greater than its distal diameter, and proximal and distal threads mounted on said outer surface of said tubular segment, wherein, the root diameter of said distal thread is greater than the crest diameter of said proximal thread, said proximal and distal threads of said hub simultaneously engage said proximal and distal threads of said collar, and said stem is sealed with said hub by rotating one of said collar and said hub substantially 180 degrees.

13. The hub of claim 10 wherein:

said threads are threaded rims of discs, each rim having dual threads.

14. A hub for mating with a catheter stem by use of a collar in a luer-type adapter, where said collar includes proximal and distal threads on an inner surface, said hub comprising:

a tubular segment which is sealed with the catheter stem, said tubular segment having an outer surface and a tapered inner surface, said tapered inner surface having a proximal diameter greater than its distal diameter, and proximal and distal threads which are mounted on said outer surface of said tubular segment, wherein, the root diameter of said distal thread is greater than the crest diameter of said proximal thread, said proximal and distal threads of said hub simultaneously engage said proximal and distal threads of said collar, and said catheter stem is placed within said tubular segment and sealed with said hub by rotating one of said collar and said hub substantially 180 degrees.

15. The hub of claim 14 wherein:

said threads are threaded rims of discs, each rim having dual threads.

\* \* \* \* \*